United States Patent [19]

Barnes et al.

[11] Patent Number: 5,430,074
[45] Date of Patent: Jul. 4, 1995

[54] GUM-COLORED DENTAL COMPOSITE AND DENTAL RESTORATION KIT

[75] Inventors: Nina Y. Barnes, Wallingford, Conn.; Ronald Feinman, Atlanta, Ga.; Samuel Waknine, Branford; Bruce H. Alpert, Madison, both of Conn.

[73] Assignee: Jeneric/Pentron, Incorporated, Wallingford, Conn.

[21] Appl. No.: 128,294

[22] Filed: Sep. 29, 1993

[51] Int. Cl.⁶ ............... A61K 6/08; A61K 8/00; A61K 13/08; C08K 3/32
[52] U.S. Cl. ................ 523/115; 523/116; 524/414; 524/416; 524/430; 524/441; 524/492; 524/495; 433/201.1; 433/199.1; 433/202.1; 433/228.1; 433/222.1; 433/203.1; 524/431; 524/556; 524/560; 524/159; 524/160
[58] Field of Search .............. 523/115, 116; 433/201.1, 199.1, 202.1, 228.1, 222.1, 203.1; 524/414, 416, 430, 441, 492, 495, 159, 160, 431, 556, 560

[56] References Cited

U.S. PATENT DOCUMENTS

| | | | |
|---|---|---|---|
| 2,205,488 | 6/1940 | Merrick | 524/560 |
| 4,649,165 | 3/1987 | Kuhlmann | 523/116 |
| 5,094,619 | 3/1992 | McLaughlin | 523/115 |

FOREIGN PATENT DOCUMENTS 0277598 8/1988 European Pat. Off. ........... 524/431

OTHER PUBLICATIONS

"The Colouring of Plastics", Chapter 9, pp. 61-63, Imperial Chemical Industries Ltd., Dyestuffs Division (1960).

*Primary Examiner*—Paul R. Michl
*Assistant Examiner*—LaVonda R. DeWitt
*Attorney, Agent, or Firm*—Watson, Cole, Grindle & Watson

[57] ABSTRACT

A gum-colored dental composite is provided which may be used in class V dental restorations or as a cosmetic coating for the gingival portion of a tooth. A kit is also provided which enables a gum-colored dental composite to be formulated which closely resembles the natural gum coloration of any patient's gums. The dental composite may be used to counter the illusion of long teeth which occurs when a gum line recedes. The dental composite may also be used on other composite resins, porcelains and metals.

14 Claims, No Drawings

GUM-COLORED DENTAL COMPOSITE AND DENTAL RESTORATION KIT

FIELD OF THE INVENTION

The present invention relates to dental composite materials made of resin and filler blends. More particularly, the present invention relates to a gum-colored dental composite which can be used in class V restorations and as a direct restorative or cosmetic coating for natural tooth surfaces, other composite resins, porcelains and metals.

BACKGROUND OF THE INVENTION

Dental filling materials have evolved from metallic fillings to porcelain compositions, and more recently to light-curable resin and filler blends. Of the light curable resins currently available, resins having cross-linkable methacrylate groups are preferred. Methacrylate resins may be blended with a filler and applied to a cleaned cavity. The resin is then light cured with a light source which provides an appropriate frequency so that monomers in the resin/filler blend crosslink to form a polymer network.

The resin/filler blends provide excellent biocompatibility, are extremely long lasting and are easy to handle. The blends are also inexpensive and are easily prepared.

Some of the more recently used methacrylate resins are bis-phenol A diglycidol methacrylate (bis-GMA), urethane dimethacrylate (UDMA), and polycarbonate dimethacrylate (PCDMA). Often, one or more of the above-identified resins is diluted with, e.g., triethylene glycol dimethacrylate (TEGDMA) or ethylmethacrylate (2-HEMA). The resin component is then mixed with fillers such as silicates, until a desired viscosity or optimal physical properties are achieved.

The resin/filler composites are useful in many dental restorations. These composites are designed to approximate natural tooth structure and are sometimes provided in kits which also include gray and yellow dyes so the restoration can be shaded to closely match the surrounding dentition.

U.S. Pat. No. 4,433,959 discloses a composite laminate dental veneer which includes color pigments of a dentin color blend. The coloring system enables the materials to closely approximate the appearance and color of a natural tooth. Tooth enamel and dentin colored blends are provided. Like other tooth-colored dental composites, the materials cannot be used to match the gum tissue of a patient as the material is white in color with shades of yellow and gray.

U.S. Pat. No. 4,521,193 discloses a method and kit for constructing dentures. The dentures include tooth-colored acrylic areas and gingival-colored acrylic areas. The temporary one-piece acrylic denture does not restore the appearance of a natural gum line but rather is used as a prosthesis.

To restore an injured tooth, a carious lesion is drilled out and the tooth is prepared to receive restorative material. A bonding agent is applied to the prepared surface and allowed to bond to the enamel and dentin. In more recent restoration kits, a light curable bonding agent is applied to the clean surface and light cured. A dental composite material is then applied to or inserted in the cavity preparation and light cured to form a restoration.

Class V cavities are those appearing on the gingival third of the facial and lingual surfaces of all teeth. Class V cavities include those at and beneath the gum line. Gum recession may occur in these areas reducing the natural gum line. Because many of these cavities appear where a patient's gums should be, it is desired to provide a gum-colored dental composite for filling cavities at or beneath the gum line. To the best of applicants' knowledge, a gum-colored dental composite has not yet been developed.

In elderly people and those suffering from periodontitus, receding gum lines have the effect of making teeth look longer by extending the clinical crown. It is desired to provide a gum-colored dental composite which can be used on the gingival third of a tooth to cosmetically restore the appearance of the natural gum line to where it was before recession of the gums occurred. Likewise, it is desirable to provide a gum-colored dental composite which can be used to cosmetically improve the appearance of a damaged gum line by its application to the gingival portion of a cavity preparation or directly onto the tooth.

SUMMARY OF THE INVENTION

The present invention provides a gum-colored dental composite useful for the restoration of class V cavities and for shortening the appearance of the clinical crown, especially on the facial surface of a tooth. The present invention also provides a cosmetic dental restoration material which can be used to counter the illusion of elongated teeth which occurs when a gum line recedes. The present invention also provides a cosmetic dental restoration material which can be used on a damaged gum line to smooth out the appearance of the gums and give the illusion of a normal gum line. The present invention also provides a kit for chair-side use by a dentist which enables the dentist to prepare a gum-colored dental composite blend having a desired matching shade of pink which can be used on the gingival portion of a tooth.

The gum-colored dental composites of the present invention comprise a mixture of one or more light-curable acrylate resins, a filler, and an amount of red or pink coloring agent sufficient to provide a pink coloration which will custom match a patient's gum color. The preferred acrylate resins used in the composites of the present invention are methacrylate resins. Of the methacrylate resins, bis-GMA, UDMA and PCDMA are preferred. The fillers of the present invention are preferably silicate fillers such as borosilicate fillers including barium borosilicate. The coloring agents used in the composites of the present invention are preferably FDA red dyes. Other coloring agents including FDA dyes may be used as modifiers to adjust the tint of the color.

The dental restoration kit of the present invention comprises a number of differently shaded pink resin composites and modifiers to achieve shades and tints which fall between the standard shades provided. An infinite number of gum-colored shades can be achieved with the kit of the present invention.

DETAILED DESCRIPTION OF THE INVENTION

The light-curable dental composite resin/filler blends of the present invention comprise at least a resin component, a filler component and a red or pink coloring agent. Trace amounts of a UV light absorber may also be added to the resin/filler blend to stabilize color. The "resin/filler blend" referred to herein includes the pink or red coloring agent and any other elements which may be used in the dental composite blend.

The resin component of the blend preferably comprises at least one acrylate resin. Preferred resins include methacrylate resins. The preferred methacrylate resins include bis-phenol A diglycidol methacrylate (Bis-GMA), urethane dimethacrylate (UDMA), and polycarbonate dimethacrylate (PCDMA). Mixtures of two or more of these methacrylate resins are also preferred. PCDMA has proven to be the most preferred of the three specific methacrylate resins and is discussed in co-pending U.S. patent application Ser. No. 07/339,097, which is herein incorporated by reference. PCDMA shrinks less than the other two resins, cures into a tougher polymer, and offers the same, if not better, biocompatibility. Other resins and mixtures of resins which are disclosed in U.S. patent application Ser. No. 339,097 may also be used in the dental composite blends of the present invention. U.S. patent application Ser. No. 339,097 is a continuation-in-part of pending application Ser. No. 195,351, filed May 12, 1988, which is a continuation of application Ser. No. 843,081, filed Mar. 27, 1986, now abandoned, which is a continuation-in-part of application Ser. No. 717,332, filed Mar. 29, 1985, also abandoned.

The resin/filler blends of the present invention preferably have a paste-like consistency so that they may be easily applied with a spatula or with fingertips. Lower viscosity blends may be applied with a syringe.

The resin component, whether a single methacrylate resin or a mixture of two or more resins, preferably has a viscosity in the range of from one to 750,000 cps at 25° C. More preferably, the resin component has a viscosity range of from 20 to 200,000 cps at 25° C. Even more preferably, the resin component has a viscosity in the range of from 60 to 120,000 cps at 25° C. While some of the methacrylate resins alone do not offer a preferred viscosity, mixtures of methacrylate resins can be blended to achieve an appropriate viscosity. Alternatively, a resin or mixture of resins can be diluted if the viscosity is too high.

Three diluents which are commonly used to dilute methacrylate resins are triethylene glycol dimethacrylate (TEGDMA), 2-hydroxy-ethylmethacrylate (2-HEMA), and benzylmethacrylate. For example, bis-GMA has a consistency similar to molasses and is much too thick to be used alone in forming a resin/filler blend. When bis-GMA is diluted in a one-to-one ratio with TEGDMA, a less viscous resin component is formed which is more easily handled when compared to bis-GMA alone, and conveniently mixes with filler to form a dental composite blend. The methacrylate diluents also polymerize during light curing to become a part of the crosslinked polymer network. The diluents have an insignificant effect on the physical properties of the cured composite. Preferably, the diluent is used in an amount of up to about 50 percent by weight of the resin component.

Resin component blends comprising between 20 and 80 percent bis-GMA and between 20 and 80 percent TEGDMA are preferred and blends comprising between 45 and 60 percent bis-GMA and between 40 and 55 percent TEGDMA are more preferred if a bis-GMA/TEGDMA mixture comprises the entire resin component. UDMA is much less viscous than bis-GMA and does not require any diluent at all; however, small amounts of TEGDMA may be added depending upon the desired viscosity of the resin component. PCDMA may also be used with or without a diluent.

While the present invention encompasses any gum-colored dental composite having a red or pink coloring agent and resembling a natural gum coloration, for most applications a resin/filler blend is used. One preferred blend comprises between about 20 and about 50 parts by weight resin component mixed with between about 50 and about 80 parts by weight filler to form 100 parts by weight of a base resin/filler blend. Depending upon the viscosity of the resin component, more or less filler may be used as a means of adjusting the viscosity of the blend. However, when greater than 80 percent by weight filler is used, the strength of the resultant restoration is sacrificed. If the filler to resin ratio is greater than 8:2, the resultant cured composite becomes too stiff for most applications. On the other hand, when over 75 percent resin component is used, the cured composite is very ductile and exhibits too little brittleness. When 50 to 80 parts by weight filler is used, the resultant cured composition tends to exhibit a preferred balance of ductility and brittleness.

Preferred fillers include silicates having an average particle size of between about 20 nanometers and about 2 microns. Borosilicates are more preferred, especially barium borosilicate.

More generally, the filler compositions of the present invention can more generally include any suitable filler which is capable of being covalently bonded to the resin matrix itself or to a coupling agent which is covalently bonded to both. Examples of suitable filling materials include, but are not limited to, silica, silicate glass, quartz, barium silicate, strontium silicate, barium borosilicate, strontium borosilicate, borosilicate, lithium silicate, amorphous silica, ammoniated or deammoniated calcium phosphate and alumina, zirconia, tin oxide and titania. Particularly suitable as fillers for dental restorative materials prepared in accordance with the present invention are those having a particle size ranging from about 0.1–5.0 $\mu$m with a silicate colloid of 0.001 to about 0.07 microns and prepared by a series of milling steps comprising wet milling in an aqueous medium, surface etch milling and silanizing milling in a silane solution. Some of the aforementioned inorganic filling materials are disclosed in U.S. Pat. Nos. 4,544,359 and 4,547,531, pertinent portions of which are incorporated herein by reference. One consideration in the selection of a filler is the difference in the index of refraction of the filler material and that of the resinous matrix. In general, a more aesthetically pleasing restoration can be obtained when the difference between the index of refraction of the filler material and that of the resin matrix is small.

The coloring agents which are preferably used in the dental composite blends of the present invention are preferably FDA approved dyes. In particular, red dyes are preferred while brown, blue and white dyes can be used as tint modifiers. Two particular red dyes that may be used are FDA red dye no. 5595, which is 95% by weight pure red iron oxide, and FDA red dye no. 40, which is 85% by weight disodium salt of 6-hydroxy-5[(2-methyl-4-sulfophenyl) azo]-2-naphthalenesulfonic acid. Red dye no. 40 and red dye no. 5595 have proven effective in providing natural gum-coloration when mixed with the dental composite blends at low levels. For example, FDA red dye no. 5595 may be used over the range of 0.001 to 0.5 percent by weight based on the weight of the resin component. More preferably, FDA red dye no. 5595 is used over the range of 0.008 to 0.22 percent by weight based on the weight of the resin component. Even at these small concentrations, the dental composites exhibit a pinkish color which closely resembles the color of natural gums. The exact amount of dye which is used may vary depending on the exact dye. What is important is that a gum-colored blend and cured composite results which closely resembles a patient's natural gum coloration. If a higher amount of resin component is used in the composite, a smaller weight percentage of red dye may be used in the resin component.

FDA red dye no. 40 may also be used over the range of 0.001 to 0.5 percent by weight based on the weight of the resin component and is preferably used over the range of from 0.0055 to 0.0295 percent by weight based on the weight of the resin component. Mixtures of red dye no. 40 and red dye no. 5595 may also be used to provide a natural gum color.

A typical gum-colored restoration kit according to the present invention is provided with more than one pink-colored base blend. For example, the kit may comprise four different dental composite blends having gum colors which can be identified as having a light tint, a medium tint, a dark tint or an extra dark tint. In order to make small adjustments in the tint, light and dark modifiers are also provided which can be mixed with the closest tint to form a composite having a color which falls between the base colors provided. A custom made blend can thus be achieved which closely resembles the specific gum pigmentation of the patient.

A light modifier may be used which contains no pigment and has a white color. This can be used with any of the base composites to lighten the base composite very slightly or to a greater degree. Any of the dental composite blends described herein may be used as the light modifier provided no pigment, or only whitening agent, is added and the modifier exhibits a substantially white coloration.

A dark modifier may be used which comprises a dental composite blend as described herein having dark pigment, such as a blue or brown pigment, added thereto. FDA blue dye no. 2 and FDA blue dye no. 5602, for example, may be added to a dental composite blend as described above to form a dark modifier. A dental composite having about 0.01 percent by weight blue dye based on the weight of the resin component may be used as a dark modifier.

FDA brown dye no. 5095 may also be used in a concentration of about 0.05 percent by weight based on the weight of the resin component to form a dark modifier. The dark modifier composite may be added to any of the base composites to darken the base composite very slightly or to a greater degree. Many combinations of modifiers and red pigments may also be provided as base composites so long as a pink coloration is achieved which closely resembles natural gingival coloration.

Other blue or brown dyes may be used over the range of 0.001 to 0.5 percent by weight based on the weight of the resin component to form dark modifiers. Other dark dyes over other ranges are not to be excluded from the scope of the present invention.

One exemplary kit according to the present invention has four base blends. The light base blend contains between about 0.0010 to about 0.0150 percent by weight red dye no. 5595 based on the weight of the resin component. A medium tint base blend contains between about 0.050 and about 0.20 percent by weight red dye no. 5595 based on the weight of the resin component. A dark blend is included which contains between about 0.050 and about 0.20 percent by weight red dye no. 5595 based on the weight of the resin component. The extra dark base blend contains between about 0.10 and about 0.30 percent by weight red dye no. 5595 based on the weight of the resin component. In addition to the four base blends, a dark modifier is provided which contains between about 0.0050 percent and about 0.0180 percent by weight FDA blue dye no. 2 based on the weight of the resin component, for example, 0.012 percent by weight blue dye no. 2 (disodium salt of 5,5'-disulfo-3-3'-dioxo-$\Delta^{2,2'}$-biindoline) based on the weight of the resin component. Alternatively, brown dye no. 5095 in an amount of between about 0.020 and about 0.060 percent by weight based on the weight of the resin component may be included in a blend to provide a dark modifier. An alternative or additional dark modifier may be provided which contains a combination of blue dyes and red dyes, for example, red dye no. 5595 at 0.2 percent by weight based on the weight of the resin component, blue dye no. 5602 (Brown iron oxide, i.e., 95% by weight pure ferric oxide —$Fe_2O_3$) at 0.01 percent by weight based on the weight of the resin component, and red dye no. 40 at 0.01 percent by weight based on the weight of the resin component. A light modifier may be provided which contains no coloring agent or only a white coloring agent.

Another exemplary kit contains a light base blend which has 0.024 percent red dye no. 40 based on the weight of the resin component. The extra dark base blend contains 0.011 percent by weight red dye no. 40 based on the weight of the resin component. The medium and dark blends contain 0.0055 and 0.0295 percent by weight red dye no. 40, respectively, based on the weight of the resin component.

In addition to these materials, the dental composite blends of the present invention may also typically include polymerization initiators, polymerization accelerators, ultraviolet light absorbers, anti-oxidants, and other additives well known in the art. Although a polymerization initiator and a polymerization accelerator are generally used in the dental composite blends, the presence of a polymerization accelerator in the composites of the present invention is optional.

The polymerization initiators usable in the blends of the present invention are conventional initiators known in the art. For example, visible light curable compositions employ light-sensitive compounds such as benzil, diketones and in particular, camphoroquinone in amounts ranging from about 0.05 to 0.5 weight percent based on the weight of the resin component. Self-curing compositions will generally contain free radical polymerization initiators such as, for example, a peroxide in amounts ranging from about 2 to about 6 weight percent based on the weight of the resin component. Particularly suitable free radical initiators are lauroyl peroxide, tributyl hydroperoxide and, more particularly benzoyl peroxide.

Preferably, light-curing is improved through the addition of trace amounts of a tertiary amine such as diethylamino ethylmethacrylate (DEAEMA). The specific combination of camphoroquinone and DEAEMA greatly accelerates light curing and need only be used in trace amounts, e.g., under 0.25 percent by weight based on the weight of the resin component.

The polymerization accelerators which may be used in the blends of the present invention are the various organic tertiary amines well known in the art. In visible light cured compositions, the tertiary amines are generally acrylate derivatives such as dimethylamino ethylmethacrylate and, particularly, diethylamino ethylmethacrylate in amounts ranging from about 0.05 to about 0.5 weight percent based on the weight of the resin component. In self-curing compositions, the tertiary amines are generally aromatic tertiary amines, such as dimethyl-p-toluidine, dihydroxyethyl-p-toluidine, and the like, in amounts ranging from about 0.05 to about 4.0 weight percent based on the weight of the resin component. These can optionally be incorporated in a pretreatment solution rather than in the otherwise completed blends.

It is preferred also to employ an ultraviolet absorber in the blends in amounts ranging from about 0.05 to about 5.0 weight percent based on the weight of the resin component. Such UV absorbers are particularly desirable in the visible light curable compositions in order to avoid discoloration of the resin from any incident ultraviolet light. Suitable UV absorbers are the various benzophenones, particularly UV-9 and UV-5411 available from American Cyanamid Company, and benzotriazoles known in the art, particularly 2-(2'-hydroxy-5'-methylphenyl)-benzotriazole, sold under the trademark TINUVIN P by Ciba-Geigy Corporation, Ardsley, N.Y.

It is also possible to use the polycarbonate dimethacrylate condensation product in resinous blends which are both self-curing and visible light curable. In this "combination" or dual cure system the resinous blend is similar to the visible light curable composition described above except for the following changes: the addition of about 0.2 to about 0.5 weight percent benzoyl peroxide based on the weight of the resin component; the addition of 0.05 to two percent by weight of dihydroxyethylparatoluidine based on the weight of the resin component; and the omission of the diethylaminoethylmethacrylate.

In one preferred embodiment of the present invention, the resinous dental composition comprises the diluent monomer TEGDMA. In a visible light curable composition including TEGDMA the resulting resin component may comprise the constituents shown in Table I below in the weight percentages shown.

TABLE I

| Broad Range | Preferred Range | More Preferred | Component |
|---|---|---|---|
| 0–80 | 15–50 | 30–40 | Urethane di-methacrylate |
| 0–60 | 15–40 | 20–30 | Polycarbonate di-methacrylate condensation product of triethylene glycol bis(chloroformate) and 2-HEMA |
| 0–60 | 15–40 | 20–30 | TEGDMA |
| 0.0–10 | 0.001–1.0 | 0.005–0.75 | Red dye FDA 40 or Red dye FDA 5595 |
| 0.0–0.50 | 0.01–0.10 | 0.02–0.06 | Brown dye FDA 5095 |
| 0.0–0.50 | 0.005–0.090 | 0.008–0.030 | Blue dye FDA 2(5602) |
| 0.0–2.0 | 0.1–1.0 | 0.2–0.8 | Tin 292 |
| 0.0–5.0 | 0.05–2.0 | 0.1–0.75 | diethylaminoethyl-methacrylate |
| 0.0–2.0 | 0.05–1.0 | 0.1–0.6 | 2, 3-d-borandione or d, 1-camphoroquinone |
| 0–1.0 | 0.001–0.1 | 0.005–0.050 | Fluorescent/whitening agent, e.g., UVITEX OB |
| 0.0–3.0 | 0.01–2.0 | 0.5–1.25 | Ultra-violet absorber e.g. UV 5411 or Tinuvin P 60 |
| 0.0–50 | 0.05–30 | 10–20 | Benzil methacrylate |
| 0.0–1.0 | 0.01–0.50 | 0.05–0.25 | Benzil | in specific amounts within these ranges to yield a 100 percent by weight resin component, The diluent 2-hydroxy-ethylmethacrylate is preferably employed in the self-cure and dual-cure resinous dental compositions in an amount of up to 50 weight percent.

Before the resin/filler blend of the present invention is applied to a cavity, a bonding agent is first applied to prime the surface. A dentin conditioner may also be applied, and if so, is used to treat the cavity preparation surface prior to applying the bonding agent. One preferred dentin condition which may be used is a blend of N-phenyl glycine and a sodium salt of benzene sulfinic acid, as disclosed in U.S. Pat. No. 5,171,149 to Alpert, which patent is incorporated herein by reference.

The bonding agent is preferably 100 percent resin component and may comprise any of the methacrylate resins discussed above. The bonding agent is light cured within the cavity to achieve about 60 to 90 percent crosslinking of the monomers in the resin. The surface of the bonding agent which is exposed to contact with the air does not become polymerized and leaves uncrosslinked sites available for crosslinking with the resin/filler blend of the invention. The kit of the present invention preferably includes a bonding agent.

Although the present invention has been described in connection with preferred embodiments, it will be appreciated by those skilled in the art that additions, modifications, substitutions and deletions not specifically described may be made without departing from the spirit and scope of the invention defined in the appended claims.

What is claimed is:

1. A dental restoration kit for filling class V cavities and restoring a damaged or receded gum line, said kit comprising in combination at least a first container, a second container, and a third container packaged together, wherein:

said first container contains therein a first dental composite comprising between about 20 and about 50 parts by weight of a first resin component and between about 50 and about 80 parts by weight filler selected from the group consisting of silica, silicate glass, quartz, barium silicate, strontium silicate, barium borosilicate, strontium borosilicate, borosilicate, lithium silicate, amorphous silica, ammoniated or deammoniated calcium phosphate, alumina, zirconia, tin oxide and titania, said first resin component comprising at least one methacrylate resin having a viscosity in the range of from one to 750,000 cps at 25° C. and between 0 and 50 percent by weight methacrylate diluent, said first dental composite further comprising a red coloring agent which remains red when said first composite is formed into a finished restoration and which is present in an amount of between 0.001 to 0.5 percent by weight based on the weight of the first resin component and sufficient to provide a finished dental restoration having a gum color which resembles natural gums;

said second container contains therein a light modifier comprising a second dental composite comprising between about 20 and about 50 parts by weight of a second resin component and between about 50 and about 80 parts by weight filler selected from the group consisting of silica, silicate glass, quartz, barium silicate, strontium silicate, barium borosilicate, strontium borosilicate, borosilicate, lithium silicate, amorphous silica, ammoniated or deammoniated calcium phosphate, alumina, zirconia, tin oxide and titania, said second resin component comprising at least one methacrylate resin having a viscosity in the range of from one to 750,000 cps at 25° C. and between 0 and 50 percent by weight diluent selected from the group consisting of triethylene glycol dimethacrylate, 2-hydroxy-ethylmethacrylate and benzylmethacrylate; and said third container contains therein a dark modifier comprising a third dental composite comprising between about 20 and about 50 parts by weight of a third resin component and between about 50 and about 80 parts by weight filler selected from the group consisting of silica, silicate glass, quartz, barium silicate, strontium silicate, barium borosilicate, strontium borosilicate, borosilicate, lithium silicate, amorphous silica, ammoniated or deammoniated calcium phosphate, alumina, zirconia, tin oxide and titania, said third resin component composite comprising at least one methacrylate resin having a viscosity in the range of from one to 750,000 cps at 25° C. and between 0 and 50 percent by weight diluent selected from the group consisting of triethylene glycol dimethacrylate, 2-hydroxy-ethylmethacrylate and benzylmethacrylate, said third dental composite further comprising at least one member selected from the group consisting of red coloring agents, blue coloring agents and brown coloring agents.

2. A dental restoration kit as in claim 1, further comprising a bonding agent to be applied to a cavity to improve bonding of a dental composite.

3. A dental restoration kit as in claim 2, wherein said bonding agent comprises a methacrylate resin having a viscosity in the range of from one to 750,000 cps at 25° C., said methacrylate resin being selected from the group consisting of bis-phenol A diglycidol methacrylate, urethane dimethacrylate and polycarbonate dimethacrylate.

4. A dental restoration kit as in claim 1, further comprising a fourth container, wherein said fourth container contains therein a fourth dental composite, and said fourth dental composite comprises between about 20 and about 50 parts by weight of a fourth resin component and between about 50 and about 80 parts by weight filler selected from the group consisting of silica, silicate glass, quartz, barium silicate, strontium silicate, barium borosilicate, strontium borosilicate, borosilicate, lithium silicate, amorphous silica, ammoniated or deammoniated calcium phosphate, alumina, zirconia, tin oxide and titania, said fourth resin component comprising at least one methacrylate resin having a viscosity in the range of from one to 750,000 cps at 25° C. and between 0 and 50 percent by weight diluent selected from the group consisting of triethylene glycol dimethacrylate, 2-hydroxy-ethylmethacrylate and benzylmethacrylate, said fourth dental composite further comprising a red coloring agent present in an amount of between 0.001 and 0.5 percent by weight based on the weight of said fourth resin and sufficient to provide said dental composite with a gum color which resembles natural gums, wherein said fourth dental composite exhibits a darker gum coloration than the gum coloration of said first dental composite.

5. A kit as defined in claim 1, wherein said methacrylate diluent is at least one member selected from the group consisting of triethylene glycol dimethacrylate, 2-hydroxy-ethylmethacrylate and benzylmethacrylate.

6. A dental restoration kit for filling class V cavities and restoring a damaged or receding gum line, said kit comprising:

a first dental composite comprising between about 20 and about 50 parts by weight of a first resin component and between about 50 and about 80 parts by weight filler selected from the group consisting of silica, silicate glass, quartz, barium silicate, strontium silicate, barium borosilicate, strontium borosilicate, borosilicate, lithium silicate, amorphous silica, ammoniated or deammoniated calcium phosphate, alumina zirconia, tin oxide and titania, said first resin component comprising at least one methacrylate resin having a viscosity in the range of from one to 750,000 cps at 25° C. and between 0 and 50 percent by weight diluent selected from the group consisting of triethylene glycol dimethacrylate, 2-hydroxy-ethylmethacrylate and benzylmethacrylate, said first dental composite further comprising a red coloring agent present in an amount sufficient to provide said first dental composite with a gum color which resembles natural gums;

a light modifier comprising a second dental composite comprising between about 20 and about 50 parts by weight of a second resin component and between about 50 and about 80 parts by weight filler selected from the group consisting of silica, silicate glass, quartz, barium silicate, strontium silicate, barium borosilicate, strontium borosilicate, borosilicate, lithium silicate, amorphous silica, ammoniated or deammoniated calcium phosphate, alumina, zirconia, tin oxide and titania, said second resin component comprising at least one methacrylate resin having a viscosity in the range of from one to 750,000 cps at 25° C. and between 0 and 50 percent by weight diluent selected from the group consisting of triethylene glycol dimethacrylate, 2-hydroxy-ethylmethacrylate and benzylmethacrylate; and a dark modifier comprising a third dental composite comprising between about 20 and about 50 parts by weight of a third resin component and between about 50 and about 80 parts by weight filler selected from the group consisting of silica, silicate glass, quartz, barium silicate, strontium silicate, barium borosilicate, strontium borosilicate, borosilicate, lithium silicate, amorphous silica, ammoniated or deammoniated calcium phosphate, alumina, zirconia, tin oxide and titania, said third resin component composite comprising at least one methacrylate resin having a viscosity in the range of from one to 750,000 cps at 25° C. and between 0 and 50 percent by weight diluent selected from the group consisting of triethylene glycol dimethacrylate, 2-hydroxy-ethylmethacrylate and benzylmethacrylate, said third dental composite further comprising at least one member selected from the group consisting of red coloring agents, blue coloring agents and brown coloring agents; and a dentin conditioner comprising at least one member selected from the group consisting of N-phenol glycine and sodium salts of benzene sulfinic acid.

7. A method of preparing a class V dental restoration comprising the steps of:

(1) providing a kit comprising:

a first dental composite comprising between about 20 and about 50 parts by weight of a first resin component and between about 50 and about 80 parts by weight filler selected from the group consisting of silica, silicate glass, quartz, barium silicate, strontium silicate, barium borosilicate, strontium borosilicate, borosilicate, lithium silicate, amorphous silica, ammoniated or deammoniated calcium phosphate, alumina, zirconia, tin oxide and titania, said first resin component comprising at least one methacrylate resin having a viscosity in the range of from one to 750,000 cps at 25° C. and between 0 and 50 percent by weight methacrylate diluent, said first dental composite further comprising a red coloring agent present in an amount of between 0.001 to 0.5 percent by weight based on the weight of the resin component and sufficient to provide the first dental composite with a gum color;

a light modifier having a lighter tint than that of said first dental composite and comprising a second dental composite comprising between about 20 and about 50 parts by weight of a second resin component and between about 50 and about 80 parts by weight filler selected from the group consisting of silica, silicate glass, quartz, barium silicate, strontium silicate, barium borosilicate, strontium borosilicate, borosilicate, lithium silicate, amorphous silica, ammoniated or deammoniated calcium phosphate, alumina, zirconia, tin oxide and titania, said second resin component comprising at least one methacrylate resin having a viscosity in the range of from one to 50,000 cps at 25° C. and between 0 and 50 percent by weight methacrylate diluent; and a dark modifier having a darker tint than that of said first dental composite and comprising a third dental composite comprising between about 20 and about 50 parts by weight of a third resin component and between about 50 and about 80 parts by weight filler selected from the group consisting of silica, silicate glass, quartz, barium silicate, strontium silicate, barium borosilicate, strontium borosilicate, borosilicate, lithium silicate, amorphous silica, ammoniated or deammoniated calcium phosphate, alumina, zirconia, tin oxide and titania, said third resin component composite comprising at least one methacrylate resin having a viscosity in the range of from one to 750,000 cps at 25° C. and between 0 and 50 percent by weight methacrylate diluent, said third dental composite further comprising at least one member selected from the group consisting of red coloring agents, blue coloring agents and brown coloring agents;

(2) preparing a cavity or lesion on the gingival third of a facial or lingual surface of a tooth to form a restoration preparation, wherein said tooth is adjacent a patient's gums and said gums have a natural gum color;

(3) comparing the natural gum color to the gum color of the first dental composite;

(4) mixing said first dental composite with at least one of said light modifier and said dark modifier to adjust the gum color of the first dental composite to more closely approximate the natural gum color and form a restorative composite;

(5) applying said restorative composite to said restoration preparation; and (6) curing said restorative composite to form a dental restoration.

8. A method as in claim 7, wherein said red coloring agent is at least one member selected from the group consisting of red iron oxides and disodium salt of 6-hydroxy-5[(2-methyl-4-sulfophenyl) azo]-2-naphthalenesulfonic acid.

9. A method as in claim 7, wherein said red coloring agent comprises red iron oxide in amount of between 0.008 and 0.22 percent by weight based on the weight of the resin component.

10. A method as in claim 7, wherein said red coloring agent comprises disodium salt of 6-hydroxy-5[(2-methyl-4-sulfophenyl)azo]-2-naphthalenesulfonic acid in amount of between 0.0055 and 0.0295 percent by weight based on the weight of the resin component.

11. A method as in claim 7, wherein said dental composite comprises between about 20 and about 50 parts by weight resin component and between about 50 and about 80 parts by weight filler, said resin component comprising at least one methacrylate resin having a viscosity in the range of from one to 750,000 cps at 25° C., said resin component also comprising between 0 and 50 percent by weight diluent selected from the group consisting of triethylene glycol dimethacrylate, 2-hydroxyethylmethacrylate and benzylmethacrylate.

12. A method as in claim 7, further comprising the step of applying a dentin conditioner to the restoration preparation prior to said step of applying the restorative composite to the restoration preparation, wherein said dentin conditioner comprises at least one member selected from the group consisting of N-phenol glycine and sodium salts of benzene sulfinic acid.

13. A method as in claim 7, further comprising the steps of comparing the gum color of the restorative composite to the natural gum color and mixing said restorative composite with at least one of said light modifier and said dark modifier to adjust the gum color of the restorative composite to match the natural gum color.

14. A method as in claim 13, further comprising the steps of comparing the gum color of the second restorative composite to the natural gum color and mixing said second restorative composite with at least one of said light modifier and said dark modifier to adjust the gum color of the restorative composite to match the natural gum color.

* * * * *